United States Patent
Shi et al.

(10) Patent No.: US 9,427,196 B2
(45) Date of Patent: Aug. 30, 2016

(54) PATIENT TABLE AND CONTROL DEVICE OF PALLET OF PATIENT TABLE

(71) Applicant: Shenyang Neusoft Medical Systems Co., Ltd., Shenyang (CN)

(72) Inventors: Xiaoping Shi, Shenyang (CN); Yang Hu, Shenyang (CN); Hong Yan, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 27 days.

(21) Appl. No.: 14/617,921

(22) Filed: Feb. 9, 2015

(65) Prior Publication Data
US 2016/0038102 A1    Feb. 11, 2016

(30) Foreign Application Priority Data

Aug. 8, 2014    (CN) .......................... 2014 1 0389957

(51) Int. Cl.
*A61B 6/04*    (2006.01)
*A61G 13/12*   (2006.01)
*A61B 6/03*    (2006.01)
(Continued)

(52) U.S. Cl.
CPC ........... *A61B 6/0457* (2013.01); *A61B 6/0407* (2013.01); *A61G 13/12* (2013.01); *A61B 5/055* (2013.01); *A61B 6/03* (2013.01); *A61B 6/032* (2013.01); *A61B 6/54* (2013.01); *H03K 17/968* (2013.01)

(58) Field of Classification Search
CPC .. A61B 6/0407; A61B 5/704; A61B 6/0457; A61B 6/032; A61B 5/055; A61B 6/03; A61B 6/54; A61G 13/12; H03K 17/968
See application file for complete search history.

(56) References Cited

U.S. PATENT DOCUMENTS 3,707,629 A * 12/1972 Colston ................ A61B 6/0457
                                                  378/176
4,803,362 A *  2/1989 Butts ..................... H03K 17/968
                                                  250/229
(Continued)

FOREIGN PATENT DOCUMENTS

CN    203424945 U    2/2014
JP    H02124144 A    5/1990
JP    H02172448 A    7/1990

OTHER PUBLICATIONS

The Chinese first Office Action issued on Dec. 17, 2015 regarding the Chinese priority patent application (APPL. No. 201410389957.X).

*Primary Examiner* — Nicholas Polito
*Assistant Examiner* — Amanda L Miller
(74) *Attorney, Agent, or Firm* — Kilpatrick Townsend & Stockton LLP

(57) ABSTRACT

A patient table and a control device of a pallet of the patient table are provided according to the present application to facilitate achieving the switching between manual operation and automatic operation in controlling the pallet, and to improve the operation convenience. The control device includes a through-beam photoelectric switch, a shutter and a trigger connected to the shutter, the trigger is arranged on a push-pull portion of the pallet to allow the shutter to be driven to move when a hand acts on the push-pull portion, to block a light beam of the through-beam photoelectric switch. The through-beam photoelectric switch is in signal connection with the control board of the patient table and is configured to send a signal for releasing the pallet to the control board of the patient table once the light beam of the through-beam photoelectric switch is blocked.

20 Claims, 6 Drawing Sheets

(51) Int. Cl.
   *H03K 17/968* (2006.01)
   *A61B 5/055* (2006.01)
   *A61B 6/00* (2006.01)

(56) References Cited

U.S. PATENT DOCUMENTS

| | | | | |
|---|---|---|---|---|
| 4,831,253 A | * | 5/1989 | Omura | H03K 17/968 200/61.02 |
| 4,984,774 A | * | 1/1991 | Zupancic | A61B 6/0457 254/122 |
| 5,721,794 A | * | 2/1998 | Uchiyama | G02B 6/353 385/16 |
| 5,952,648 A | * | 9/1999 | Worm | H01L 31/167 250/222.1 |
| 6,045,262 A | | 4/2000 | Igeta et al. | |
| 2001/0019602 A1 | * | 9/2001 | Nakajo | G03B 42/025 378/209 |
| 2010/0171026 A1 | * | 7/2010 | Saitou | H03K 17/968 250/221 |

* cited by examiner

PATIENT TABLE AND CONTROL DEVICE OF PALLET OF PATIENT TABLE

This application claims the benefit of priority to Chinese patent application No. 201410389957.X titled "PATIENT TABLE AND CONTROL DEVICE OF PALLET OF PATIENT TABLE" and filed with the Chinese State Intellectual Property Office on Aug. 8, 2014, which is incorporated herein by reference in its entirety.

TECHNICAL FIELD

The present application relates to the technical field of medical equipment, and particularly to a patient table and a control device of a pallet of the patient table.

BACKGROUND

With the development of science and technology, a medical computed tomography (CT) machine has been increasingly applied in clinical medicine, and plays an important role in medical diagnosis and treatment. Currently, the medical CT machine has become one of the main medical diagnostic equipment. A patient table, as an important component of the medical CT machine, is also increasingly applied.

Reference is made to FIGS. 1 and 2. FIG. 1 is a schematic view showing the structure of a patient table in the conventional technology in a state that a pallet thereof extends out of the patient table; and FIG. 2 is a schematic view of the patient table shown in FIG. 1 in a state that the pallet thereof is retracted.

When performing a CT scanning, a patient lies on a pallet 11' of a patient table 1'. The pallet 11' is capable of extending and retracting with respect to a frame 12', to move the patient. Under normal circumstances, the extending and retracting movement of the pallet 11' is automatic, however, in some circumstances, it is required to push and draw the pallet 11' manually, that is, the movement state of the pallet 11' is required to be switched from automatic operation to manual operation. In the conventional technology, the switching between automatic operation and manual operation is controlled by an on-off switch 2', in detail, once the on-off switch 2' is pressed, a motion signal is transmitted to a control board of the patient table through a cable connected to the on-off switch 2', and once receiving a switching signal, the control board of the patient table sends a control signal to control the pallet 11' to stop the automatic extending and retracting movement. This process is also referred to as a pallet releasing process.

Generally, the on-off switch 2' is fixedly mounted on a side of a tail portion of the patient table 1', that is, the on-off switch 2' does not move along with the pallet 11'. If a doctor intends to release the pallet 11', the doctor has to press the on-off switch 2' first. However, in practice, the doctor usually does not stand at the tail portion of the pallet, thus, the doctor needs to move to the tail portion of the pallet first to press the on-off switch 2' and then pushes and pulls a handle of the pallet to perform the manual operation of pulling and drawing the pallet 11'. That is, the switching between automatic operation and manual operation requires two steps. Particularly, in a case that the pallet 11' extends out by a great distance to a position far away from the on-off switch 2', it is very inconvenient for the doctor to operate. Meanwhile, mounting the on-off switch 2' on both sides may increase the difficulty of assembling and positioning and also may adversely affect an overall appearance of the patient table.

Accordingly, a technical issue to be addressed presently by those skilled in the art is to innovatively design a patient table and a control device of a pallet of the patient table to simplify the switching between automatic operation and manual operation in control process of the pallet.

SUMMARY

A control device of a pallet of a patient table is provided according to an aspect of the present application, which may facilitate achieving the switching between automatic operation and manual operation in controlling the pallet, and improve the operation convenience.

A patient table including the control device is further provided according to another aspect of the present application, and a pallet of the patient table may be used more flexibly.

To address the above technical issues, a control device of a pallet of a patient table is provided according to the present application, the patient table has a control board for controlling movement of the patient table, and the pallet of the patient table has a manually operated push-pull portion, the control device includes a through-beam photoelectric switch, a shutter and a trigger connected to the shutter, the trigger is arranged on the push-pull portion to allow the shutter to be driven to move when a hand acts on the push-pull portion, to block a light beam of the through-beam photoelectric switch; the through-beam photoelectric switch is in signal connection with the control board of the patient table and is configured to send a signal for releasing the pallet to the control board of the patient table once the light beam of the through-beam photoelectric switch is blocked.

The control device according to the present application is provided with a through-beam photoelectric switch, and is provided with a trigger on the push-pull portion of the pallet, hence, when it is required to manually push or pull the pallet, the trigger may be activated by simply acting on the push-pull portion with a hand, so as to drive the shutter to block a light beam of the through-beam photoelectric switch, and a signal for releasing the pallet is sent to the control board of the patient table by the through-beam photoelectric switch. Compared with the on-off switch arranged on a tail portion of the pallet in the conventional technology, the trigger according to the present application is movable along with the push-pull portion of the pallet, and when an operator acts on the push-pull portion, the switching between manual operation and automatic operation of the pallet may be achieved at the same time, and the operator does not need to move to the tail portion of the pallet to press the on-off switch, thereby improving the operation convenience and the operation efficiency. Compared with the on-off switch in the conventional technology, the through-beam photoelectric switch in the present application has a simple structure without being connected to a cable, therefore the assembly and use is more convenient.

Preferably, the trigger is embedded in the push-pull portion and has a gripping portion extending out of the push-pull portion, and the gripping portion is connected to the shutter.

In a case that the trigger is provided with a gripping portion, the shutter may be driven to block the light beam when a hand grips the push-pull portion, and then a signal for releasing the pallet is sent to the control board of the patient table by the through-beam photoelectric switch, such that a hand may grip the push-pull portion to push and pull the pallet after the pallet stops moving automatically, thereby achieving the manual control of the pallet.

Preferably, the gripping portion is connected to the shutter via an elastic member, to generate an elastic force under the action of a gripping force to drive the shutter to move.

Meanwhile, the gripping portion may also be connected to the shutter via an elastic member, such that an elastic force applied on the elastic member by the gripping force may drive the shutter to move, without arranging a complicated transmission structure. Also, the stroke of the shutter may be controlled by the magnitude of the griping force, to block the light beam effectively.

Preferably, the elastic member is an elastic connecting rod inserted in the push-pull portion, and the elastic connecting rod has a top end connected to the gripping portion and a bottom end connected to the shutter via a wire rope.

Preferably, the shutter includes a stationary plate and a movable plate which both has a through hole for the light beam of the through-beam photoelectric switch to pass through; and the movable plate is connected to the trigger, and is movable under the actuation of the trigger to allow the through hole of the movable plate to be misaligned with the through hole of the stationary plate to block the light beam of the through-beam photoelectric switch.

The shutter may include a stationary plate and a movable plate which both has a through hole for the light beam to pass through. The light beam can pass through normally when the through holes of the two plates are aligned with each other, and the through-beam photoelectric switch will not send a signal to the control board of the patient table. If it is required to manually control the pallet to move, the through hole of the movable plate may be misaligned with the through hole of the stationary plate by simply driving the movable plate to move, thus the light path may be blocked to block the light beam and change the state of the through-beam photoelectric switch. In the whole control process, the displacement of the movable plate is small and thus the required driving force and motion space are both small, thereby simplifying the structure and improving the operation efficiency.

Preferably, the movable plate has one end connected to the trigger and the other end connected to a return spring for driving the movable plate back to its original position.

The return spring may generate an elastic deformation in a process that the trigger drives the movable plate to move. When the trigger stops acting, the return spring will generate an elastic return force to bring the movable plate to return to the original position, to align the through hole of the movable plate with the through hole of the stationary plate, thus the light beam can pass through normally, and the pallet is recovered to the state of automatic control.

Preferably, the shutter further includes a position-limiting member for limiting a stroke of the movable plate, to prevent the movable plate from moving beyond the limit position and improve the operation reliability.

Preferably, the position-limiting member is a position-limiting groove in cooperation with the movable plate, and the through hole of the movable plate is aligned with the through hole of the stationary plate when the movable plate abuts against one end of the position-limiting groove, and is misaligned with the through hole of the stationary plate when the movable plate abuts against the other end of the position-limiting groove.

The position-limiting groove has a simple structure and is capable of effectively controlling the movement of the movable plate, thereby preventing the movable plate from moving beyond the limit position and improving the reliability and stability of the control.

Preferably, the through-beam photoelectric switch includes a light projector and a light receiver, and the light projector and the light receiver are respectively arranged at two ends of a frame.

A patient table is further provided according to the present application, and includes a frame and a pallet arranged on the frame, wherein the pallet is controlled by the control device of the pallet of the patient table according to any one of the above solutions.

Since the patient table according to the present application has the control device according to any one of the above solutions, the patient table according to the present application also has the technical effects generated by the control device according to any one of the above solutions, which will not be described herein.

Figure 1:
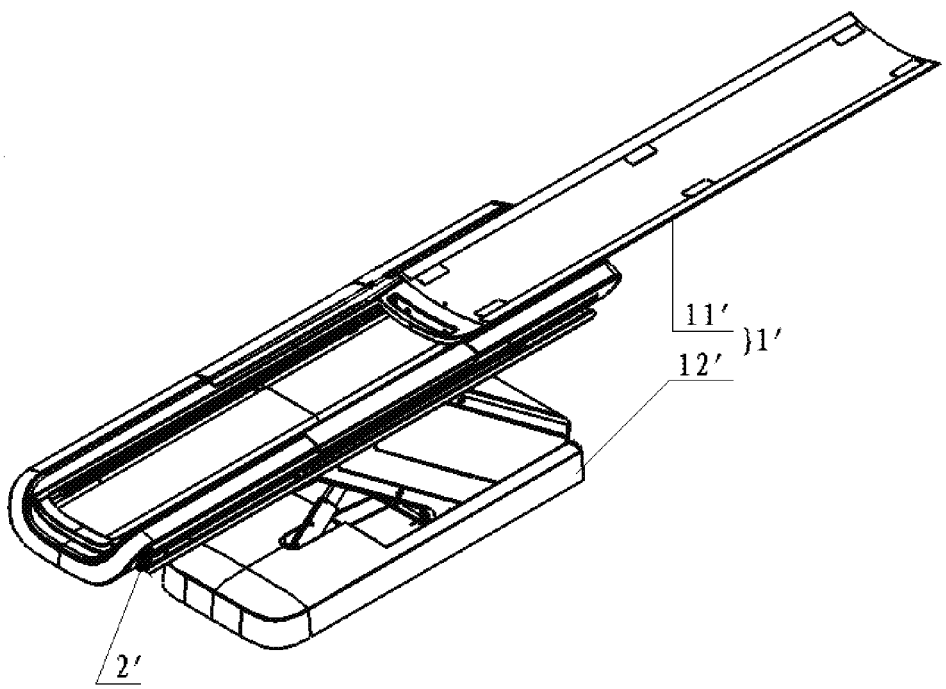
FIG. 1 is a schematic view showing the structure of a patient table in the conventional technology in a state that a pallet thereof extends out of the patient table.
Figure 2:
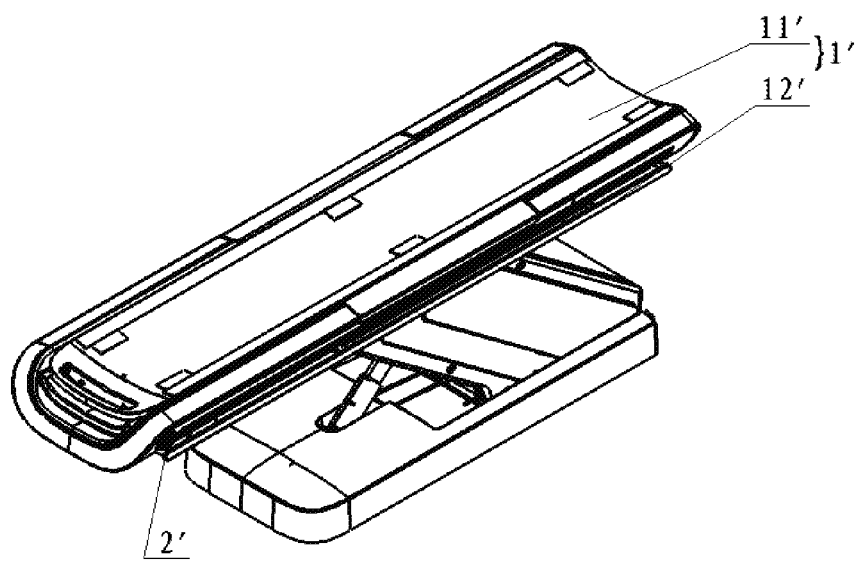
FIG. 2 is a schematic view of the patient table shown in FIG. 1 in a state that the pallet thereof is retracted.

Reference Numerals in FIGS. 1 and 2:

| 1' patient table, | 11' pallet, |
| 12' frame, | 2' on-off switch. |

Figure 3:
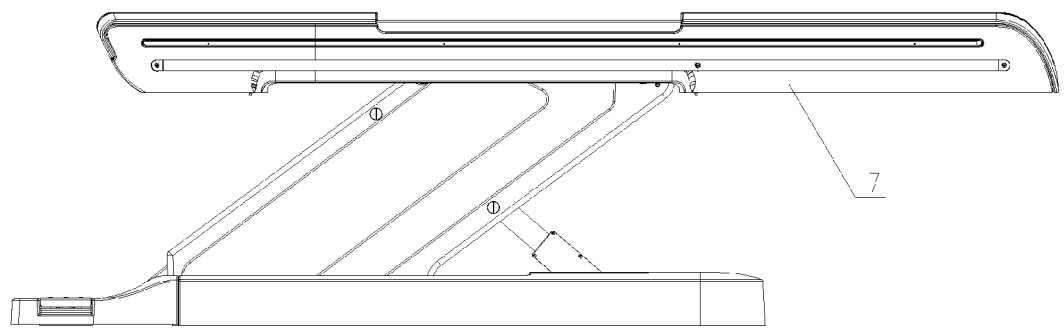
FIG. 3 is a front schematic view showing the structure of a patient table according to an embodiment of the present application.
Figure 11:
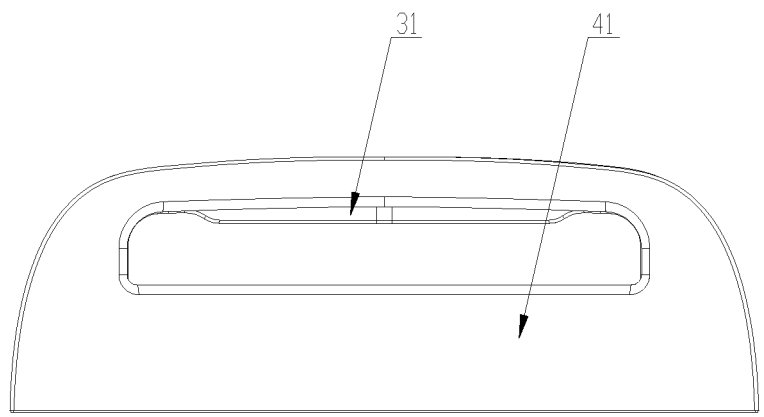
FIG. 11 is a schematic view showing an external structure of the push-pull portion according to the present application, with the trigger embedded therein.

Reference Numerals in FIGS. 3 and 11:

| 1 through-beam photoelectric switch, | 11 light projector, |
| 12 light receiver, | 2 shutter, |
| 21 stationary plate, | 22 movable plate, |
| 23 return spring, | 24 position-limiting member; |
| 3 trigger, | 31 gripping portion; |

-continued

| | |
|---|---|
| 4 pallet, | 41 push-pull portion; |
| 5 elastic member; | 6 wire rope; |
| 7 frame; and | 8 connector. |

DETAILED DESCRIPTION

A control device of a pallet of a patient table is provided according to an aspect of the present application, to facilitate achieving the switching between automatic operation and manual operation in controlling the pallet, and improve the operation convenience.

A patient table including the above control device is provided according to another aspect of the present application, and a pallet of the patient table may be more flexibly used.

For those skilled in the art to better understand technical solutions of the present application, the present application is described in detail hereinafter in conjunction with drawings and embodiments.

Figure 4:
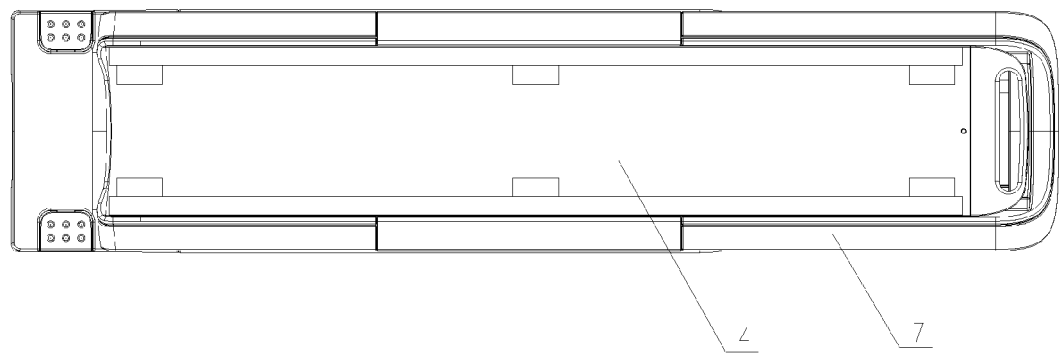
FIG. 4 is a top view of the patient table shown in FIG. 3.

Reference is made to FIGS. 3 and 4. FIG. 3 is a front schematic view showing the structure of a patient table according to an embodiment of the present application; and FIG. 4 is a top view of the patient table shown in FIG. 3.

As shown in FIG. 3, a patient table according to the present application includes a frame 7 and a pallet 4 arranged on the frame 7. The pallet 4 is movable automatically with respect to the frame 7 under the control of a control board of the patient table, to carry a patient on the pallet 4 to perform a CT scanning, that is, the patient table includes a control board for controlling the movement of the patient table. However, in scanning, some special circumstances may happen, for example, the position of the patient is deviated from the scanning location, or the patient is stuck. Under the above circumstances, it is required to stop the automatic movement of the pallet 4 and manually control a push-pull portion 41 of the pallet 4 to manually push and pull the pallet 4 to move, so as to better adjust the position of the pallet 4. In the conventional technology, the push-pull portion 41 is generally a pallet handle which has a simple structure and is easily to grip. Certainly, the push-pull portion 41 may be embodied as, by those skilled in the art, a pit for placing a hand or other structures for ease of griping, and is not limited to the pallet handle. Certainly, any portions to which an acting force is manually applied may form the push-pull portion 41.

Figure 5:
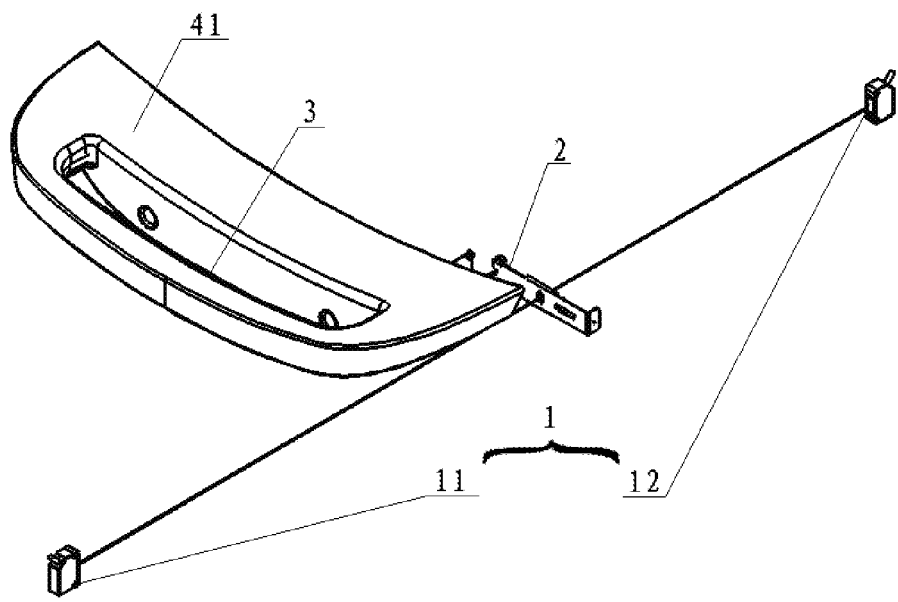
FIG. 5 is a schematic view showing the structure of a control device of a pallet of the patient table according to an embodiment of the present application.
Figure 6:
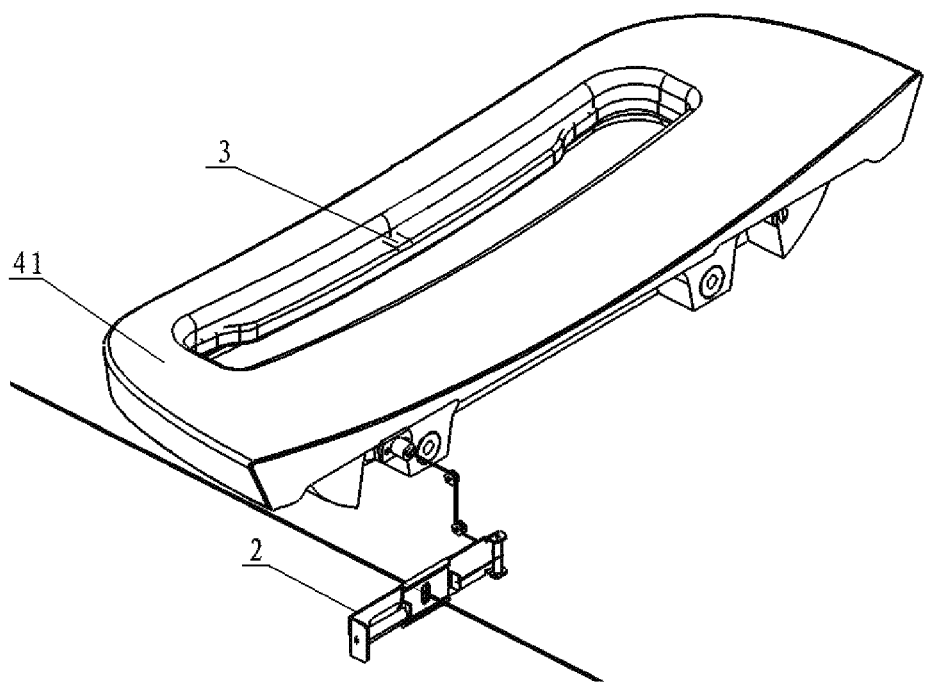
FIG. 6 is a schematic view showing the structure of a shutter and a trigger in an arrangement manner according to the present application when a light beam is not blocked.
Figure 7:
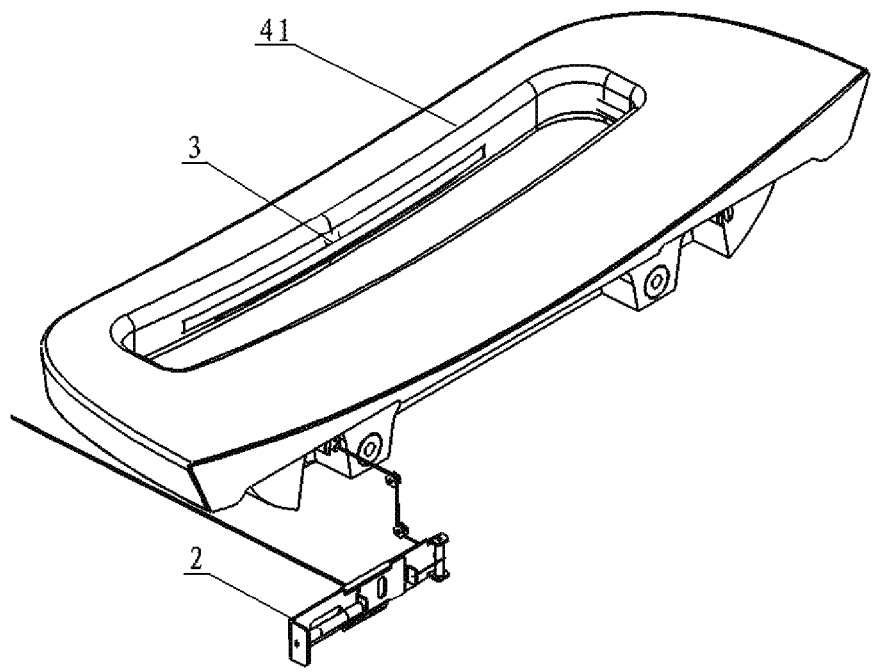
FIG. 7 is a schematic view showing the structure of the shutter and the trigger in an arrangement manner according to the present application when the light beam is blocked.

A control device of a pallet of a patient table is further provided according to the present application, to control the pallet of the patient table to achieve the switching between automatic operation and manual operation. Reference is made to FIGS. 5 to 7, FIG. 5 is a schematic view showing the structure of the control device of the pallet of the patient table according to an embodiment of the present application; FIG. 6 is a schematic view showing the structure of a shutter and a trigger in an arrangement manner according to the present application when a light beam is not blocked; and FIG. 7 is a schematic view showing the structure of the shutter and the trigger in an arrangement manner according to the present application when the light beam is blocked.

The control device of the pallet of the patient table according to the present application includes a through-beam photoelectric switch 1, a shutter 2 and a trigger 3. The trigger 3 is arranged on the push-pull portion 41 of the pallet 4 and is connected to the shutter 2. The trigger 3 is activated when a hand acts on the push-pull portion 41, thus the trigger 3 drives the shutter 2 to move to block a light beam of the through-beam photoelectric switch 1. The through-beam photoelectric switch 1 is in signal connection with the control board of the patient table, and once the light beam thereof is blocked, the through-beam photoelectric switch 1 sends a signal for releasing the pallet 4 to the control board of the patient table, and once receiving the signal, the control board of the patient table controls the pallet 4 to stop the automatic movement, thereby achieving the releasing of the pallet 4.

The signal connection refers to a connection manner for transmitting signal by wire connection or wireless connection.

In the control device according to the present application, the trigger 3 is arranged on the push-pull portion 41 of the pallet 4, and when it is required to manually operate the pallet 4, the trigger 3 may be activated by a hand acting on the push-pull portion 41, to drive the shutter 2 connected to the trigger 3 to move, and the light beam of the through-beam photoelectric switch 1 may be blocked by the shutter 2. Therefore, compared with the conventional technology using an on-off switch for controlling, in the present application, when it is required to push and pull the pallet 4, the releasing of the pallet 4 may be achieved by directly acting on the push-pull portion 41 without further acting on the on-off switch, thus the present application has a simple structure, is easy to operate, simplifies the operation process and improves the operation efficiency. The through-beam photoelectric switch 1 has a high reaction sensitivity, and may send a signal to the control board of the patient table rapidly once the light beam of the through-beam photoelectric switch 1 is blocked. Therefore, the releasing of the pallet 4 may be rapidly achieved once a hand acts on the push-pull portion 41, that is, by integrating the trigger 3 with the push-pull portion 41, the releasing of the pallet 4 may be achieved simultaneously when the pallet 4 is pulling.

The shutter 2 may also be arranged on the pallet 4 to move along with the pallet 4. In this way, in the moving process of the pallet 4, the trigger 3 is stationary with respect to the shutter 2, thereby simplifying the connection structure of the trigger 3 and the shutter 2.

The shutter 2 may also be arranged at a position close to the push-pull portion 41, or a distance between the shutter 2 and the push-pull portion 41 is within a predetermined range, the predetermined range is configured as a small value to reduce a distance between the shutter 2 and the trigger 3, thereby improving the movement reliability and the actuation accuracy. For example, as shown in FIGS. 5 to 7, the shutter 2 may be arranged on a side of the pallet 4 at a position close to the push-pull portion 41 of the pallet 4; and as shown in FIGS. 3 and 4, the shutter 2 may be arranged inside the frame 7 to simplify the external structure of the whole patient table and reduce the difficulty in assembling and positioning the patient table.

Furthermore, the through-beam photoelectric switch 1 may include a light projector 11 and a light receiver 12, as shown in FIG. 5. The light projector 11 and the light receiver 12 may be arranged respectively at two ends of the frame 7. Thus, in the entire moving process of the pallet 4, since the pallet 4 is always on the frame 7 no matter where the pallet 4 retracts to, whether releasing the pallet 4 or not may be controlled by whether the light beam between the light projector 11 and the light receiver 12 is blocked or not.

To simplify the structure, the light projector 11 and the light receiver 12 may be fixedly arranged on the frame 7 and do not move along with the pallet 4, thus a problem, that a cable connected to the light projector 11 and the light receiver 12 moves along with the light projector 11 and the light receiver 12, will not occur. The light projector 11 may emit a light beam to the light receiver 12 continuously, and the light receiver 12 is configured to receive the light beam emitted by the light projector 11, and a trigger actuator built in the light receiver 12 is activated once the light beam is blocked and then outputs a signal for releasing the pallet 4, and the signal is transmitted to the control board of the patient table, therefore achieving the releasing of the pallet 4.

The shutter 2 may be a baffle. When the pallet 4 is moving automatically, the shutter 2 is located at a position away from a light path of the through-beam photoelectric switch 1, that is, the light beam will not be blocked by the shutter 2. When the pallet 4 is required to be switched from automatic operation to manual operation, a hand acts on the push-pull portion 41, to drive the shutter 2 to move through the trigger 3, such that the shutter 2 moves to the light path of the through-beam photoelectric switch 1 and blocks the light beam, thereby enabling the through-beam photoelectric switch 1 to send the signal for releasing the pallet 4 to the control board of the patient table.

It should be appreciated by those skilled in the art that, when the light beam is no longer blocked by the shutter 2, that is, the light beam of the through-beam photoelectric switch 1 is not blocked, the control board of the patient table does not control the pallet 4 to be released, thus the pallet 4 at this time is recovered to the automatic moving state. In other words, when the light beam is released by the shutter 2 (i.e. the light beam is not blocked by the shutter 2), the through-beam photoelectric switch 1 sends a signal to the control board of the patient table, to enable the control board of the patient table to control the pallet 4 to move automatically. Certainly, a return switch in signal connection with the control board of the patient table may be arranged additionally, to allow the pallet 4 to recover to the automatic moving state.

The shutter 2 may also be configured as two baffles which both have a through hole and are movable with respect to each other. When the through holes of the two baffles are aligned with each other, the light beam of the through-beam photoelectric switch 1 may be emitted through the through holes, that is, the light beam passes through the baffles normally without being blocked. When it is required to block the light beam to change the state of the through-beam photoelectric switch 1, it is only required to drive one baffle to move to misalign the through holes of the two baffles, thus the path of the light beam can be blocked.

Figure 8:
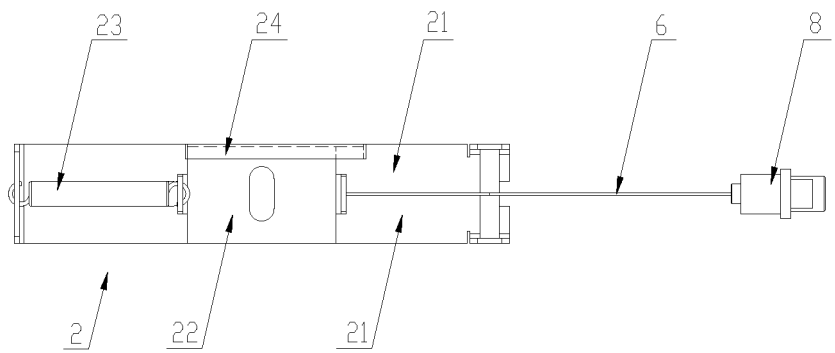
FIG. 8 is a schematic view showing the structure of the shutter in an arrangement manner according to the present application.

The shutter 2 according to the present application is described in detail hereinafter in conjunction with drawings. Reference is made to FIG. 8, which is a front schematic view showing the structure of the shutter in an arrangement manner according to the present application.

The shutter 2 may include a stationary plate 21 and a movable plate 22 which both has a through hole for the light beam of the through-beam photoelectric switch 1 to pass through, and the movable plate 22 is connected to the trigger 3. The trigger 3 is able to drive the movable plate 22 to move, to allow the through hole of the movable plate 22 to be misaligned with the through hole of the stationary plate 21, thereby blocking the light beam and changing the state of the through-beam photoelectric switch 1.

With the above structure, the shutter 2 may be arranged in the light path of the through-beam photoelectric switch 1. Under normal circumstances, the through holes of the stationary plate 21 and the movable plate 22 are aligned with each other, to allow the light beam of the through-beam photoelectric switch 1 to pass through, as shown in FIG. 6. When it is required to release the pallet 4, a hand acts on the push-pull portion 41 to activate the trigger 3 and to drive the movable plate 22 to move by the trigger 3, to misalign the through hole of the movable plate 22 with the through hole of the stationary plate 21 to block the path of the light beam, i.e. to block the light beam, thereby changing the state of the through-beam photoelectric switch 1 and sending a signal for releasing the pallet 4 to the control board of the patient table, as shown in FIG. 7.

When the shutter 2 is embodied as the structure having the stationary plate 21 and the movable plate 22, the shutter 2 may be located on a side of the pallet 4 and in the light path of the through-beam photoelectric switch 1. When it is required to block the light beam, it is only required to move the movable plate 22 by the trigger 3, and the driving force and the transmission structure required are relatively simple. Meanwhile, the stationary plate 21 may be fixedly mounted on the pallet 4, and it is only required to arrange a transmission component and a positioning structure of the movable plate 22, thereby improving the positioning reliability and reducing the positioning difficulty. In another aspect, when the stationary plate 21 is fixed, the stationary plate 21 may be taken as a reference when the movable plate 22 is driven to move, to control the movement of the movable plate 22, thereby improving the operation precision. Moreover, since diameters of the through holes of the stationary plate 21 and the movable plate 22 are both small, the movable plate 22 is only required to move a small distance to misalign the through hole of the movable plate 22 with the through hole of the stationary plate 21, thus the movable plate has a high movement reliability, and the blocking of the light beam may be realized rapidly and accurately, thereby improving efficiency.

It may be conceived that, the shutter 2 may be embodied as other structures, for example, a component that can block the light beam, such as a block piece and etc. Reference can be made to the conventional technology, which will not be described herein.

On this basis, one end of the movable plate 22 may be connected to the trigger 3, and the other end of the movable plate 22 may be connected to a return spring 23. When the movable plate 22 is driven by the trigger 3 to move, the return spring 23 is compressed or stretched to be deformed. When the trigger 3 stops acting on the movable plate 22, the return spring 23 generates a moving tendency for deformation restoring, and in turn pushes or pulls the movable plate 22 to return to the original position by the elastic restoring force, thus the through hole of the movable plate 22 is aligned with the through hole of the stationary plate 21, to stop blocking the light beam, and the shutter 2 returns to the state shown in FIG. 6.

In other words, the movable plate 22 may be provided with a return structure, for example, an elastic restoring component, such as the above return spring 23 and etc. In this case, in one aspect, it won't interfere in the trigger 3 driving the movable plate 22 to move, and in another aspect, it may achieve the returning of the movable plate 22 automatically when the trigger 3 stops driving the movable plate 22. The return structure has a simple structure and is more convenient to use.

Furthermore, for preventing the return spring 23 and other structures from being driven beyond the limit and improving the reliability of controlling the movable plate 22, a position-limiting member 24 may be further provided, to restrict a stroke of the movable plate 22 and assist in positioning the movable plate 22 to a position where the through hole of the movable plate 22 is misaligned or aligned with the through hole of the stationary plate 21, thereby avoiding the movement of the movable plate 22 beyond the limit position, and in turn improving the movement reliability of the movable plate 22.

The position-limiting member 24 may be position-limiting baffles arranged at two limits of the movement of the movable plate 22, or may be a position-limiting groove as shown in FIG. 8. The position-limiting member 24 may be configured as a position-limiting groove in cooperation with the movable plate 22, in this case, the movable plate 22 is movable along the position-limiting groove whether the movable plate 22 is driven by the trigger 3 to move or is driven by the return spring 23 to return to the original position, and the through hole of the movable plate 22 is aligned with the through hole of the stationary plate 21 when the movable plate 22 abuts against one end of the position-limiting groove, and is misaligned with the through hole of the stationary plate 21 when the movable plate 22 abuts against the other end of the position-limiting groove. In detail, as shown in FIG. 8, when the movable plate 22 abuts against an end of the position-limiting member 24 that is close to the return spring 23, the through hole of the movable plate 22 is aligned with the through hole of the stationary plate 21, thus the light beam can pass through, as shown in FIG. 6. When the movable plate 22 is driven by the trigger 3 to move to a position abutting against an end of the position-limiting member 24 that is away from the return spring 23, the through hole of the movable plate 22 is misaligned with the through hole of the stationary plate 21, thus the light beam is blocked, as shown in FIG. 7.

Figure 9:
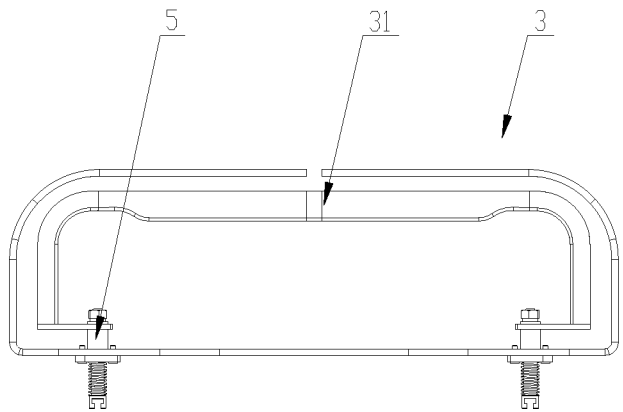
FIG. 9 is a front schematic view showing the structure of the trigger in an arrangement manner according to the present application.
Figure 10:
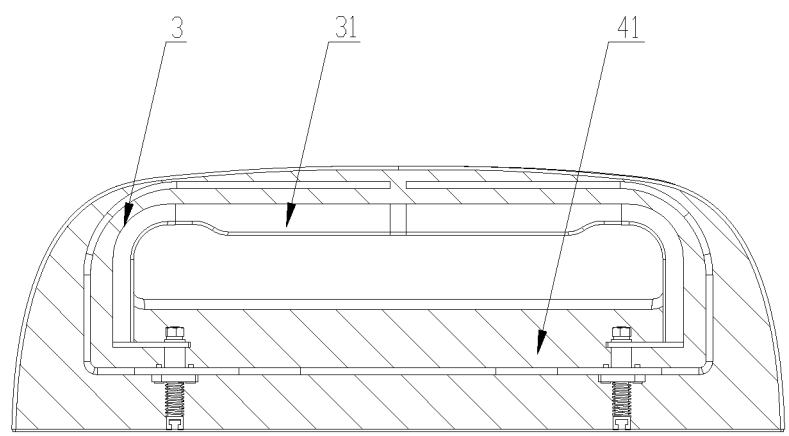
FIG. 10 is a sectional schematic view showing the structure of a push-pull portion with the trigger shown in FIG. 9 embedded therein.

Reference is made to FIGS. 9 to 11. FIG. 9 is a front schematic view showing the structure of the trigger in an arrangement manner according to the present application; FIG. 10 is a sectional schematic view showing the structure of a push-pull portion with the trigger shown in FIG. 9 embedded therein; and FIG. 11 is a schematic view showing an external structure of the push-pull portion according to the present application, with the trigger embedded therein.

The trigger 3 according to the present application may be a manually operated handle. When a hand acts on the push-pull portion 41, the manually operated handle may be activated to drive the shutter 2 connected to the manually operated handle to move, which facilitates manual operation.

In detail, the manually operated handle may be arranged inside the push-pull portion 41, and may be provided with a gripping portion 31 extending out of the push-pull portion 41, and the gripping portion 31 may be connected to the shutter 2 via an elastic member 5. In a case that the push-pull portion 41 is a pallet handle, the gripping portion 31 extends out of the pallet handle, thus when the pallet handle is gripped by an operator, the acting force also applies on the gripping portion 31, thus the gripping portion 31 causes the elastic member 5 connected to the gripping portion 31 to generate an elastic deformation, to allow the elastic member 5 to generate an elastic force for driving the shutter 2 to move, as shown in FIG. 9.

Certainly, the gripping portion 31 may also be connected to the shutter 2 via other connecting members which are not limited to the elastic member 5 and can be any structures as long as it can realize force transmission. For example, the connecting member may be a tension rod, a chain and etc.

Furthermore, the elastic member 5 may be an elastic connecting rod inserted in the push-pull portion 41, as shown in FIG. 10. The elastic connecting rod has a top end connected to the gripping portion 31, and a bottom end connected to the shutter 2 by a wire rope 6. As shown in FIGS. 5 to 7, the wire rope 6 may be provided with a guide wheel to change the direction of the wire rope 6, thereby facilitating connecting the shutter 2 to the trigger 3. Meanwhile, the flexible wire rope 6 requires a small installation space and has a light weight, which may better meet the requirements for mounting the pallet handle.

It is conceivable that for those skilled in the art, the bottom end of the elastic connecting rod may extend out of the pallet handle and then a connecting portion may be provided at the bottom end of the elastic connecting rod, and the wire rope 6 is connected to a connector 8. The connection between the wire rope 6 and the elastic connecting rod is achieved by the connector 8, as shown in FIGS. 8 and 9, and the connector 8 has one end connected to the wire rope 6, and the other end for connecting the elastic connecting rod.

It is to be noted that for ease of description, the wire rope 6 is indicated as a linear structure in FIG. 8. However, it should be appreciated by those skilled in the art that, in order to achieve the connection between the shutter 2 and the trigger 3, a guide wheel may be provided to change the extending direction of the wire rope 6, as shown in FIGS. 5 to 7.

Furthermore, it should be further appreciated by those skilled in the art that, the structure of the trigger 3 is various and is not limited to the above manually operated handle. For example, the trigger 3 may also be a trigger switch or other components for transmitting force. Certainly, the connecting component for the shutter 2 and the trigger 3 is not limited to the elastic connecting rod, and may also be other connecting-rod transmission components or flexible connecting members, as long as it can transmit the manual force acting on the trigger 3 to the shutter 2.

Furthermore, for ease of description, other structures of the patient table are omitted in FIGS. 5 to 7, only the push-pull portion 41 of the pallet 4 and the control device according to the present application are illustrated, in which, the straight line between the light projector 11 and the light receiver 12 indicates the light beam. The pallet handle (i.e. the push-pull portion 41) and the trigger 3 are positioned vertically in FIGS. 9 and 10, that is structural views of the pallet handle in FIGS. 5 to 7 being turning upward by 90 degree. Thus the bottom of the elastic connecting rod and an end of the elastic connecting rod that is connected to the shutter 2, or a portion of the elastic connecting rod facing downward in FIG. 9 may be understood as a portion away from the gripping portion 31.

Furthermore, since a large portion of the trigger 3 and the shutter 2 are arranged inside the pallet 4 or the frame 5, they cannot be shown in the external structural views in FIGS. 3 and 4, but this should not be interpreted as that the pallet according to the present application is the same as the pallet in the conventional technology. As illustrated clearly in FIGS. 3 and 4, the pallet according to the present application does not include an on-off switch, and the whole structure of the patient table is simplified. Of course, the patient table has a complicated structure, only the control device of the pallet of the patient table is described in detail herein, other portions that are not described may refer to the conventional technology, which will not be described herein.

It is to be noted that, the control device of the pallet of the patient table according to the present application is not limited to be applied in an X-ray computed tomography device, i.e. a CT patient table, may also be applied to a medical device similar to the CT patient table, which includes but is not limited to the follow devices: an X-ray positron emission tomography-computed tomography (PET-CT, including a positron emission tomography, i.e. PET), a medical electronic linear accelerator (LA), and a medical nuclear magnetic resonance imaging equipment (MRI).

A patient table and a control device of a pallet of the patient table according to the present application are described in detail hereinbefore. The principle and the embodiments of the present application are illustrated herein by specific examples. The above description of examples is only intended to help the understanding of the idea of the present application. It should be noted that, for the person skilled in the art, a few of modifications and improvements may be made to the present application without departing from the principle of the present application, and these modifications and improvements are also deemed to fall into the scope of the present application defined by the claims.

The invention claimed is:

1. A control device of a pallet of a patient table, the patient table having a control board for controlling movement of the patient table, and the pallet of the patient table having a manually operated push-pull portion, wherein the control device comprises a through-beam photoelectric switch, a shutter and a trigger connected to the shutter, the trigger is arranged on the push-pull portion to allow the shutter to be driven to move when a hand acts on the push-pull portion, to block a light beam of the through-beam photoelectric switch; the through-beam photoelectric switch is in signal connection with the control board of the patient table and is configured to send a signal for releasing the pallet to the control board of the patient table once the light beam of the through-beam photoelectric switch is blocked.

2. The control device according to claim 1, wherein the trigger is embedded in the push-pull portion and has a gripping portion extending out of the push-pull portion, and the gripping portion is connected to the shutter.

3. The control device according to claim 2, wherein the gripping portion is connected to the shutter via an elastic member, to generate an elastic force under the action of a gripping force to drive the shutter to move.

4. The control device according to claim 3, wherein the elastic member is an elastic connecting rod inserted in the push-pull portion, and the elastic connecting rod has a top end connected to the gripping portion and a bottom end connected to the shutter via a wire rope.

5. The control device according to claim 1, wherein the shutter comprises a stationary plate and a movable plate which both has a through hole for the light beam of the through-beam photoelectric switch to pass through; and the movable plate is connected to the trigger, and is movable under the actuation of the trigger to allow the through hole of the movable plate to be misaligned with the through hole of the stationary plate to block the light beam of the through-beam photoelectric switch.

6. The control device according to claim 5, wherein the movable plate has one end connected to the trigger and the other end connected to a return spring for driving the movable plate back to its original position.

7. The control device according to claim 6, wherein the shutter further comprises a position-limiting member for limiting a stroke of the movable plate.

8. The control device according to claim 7, wherein the position-limiting member is a position-limiting groove in cooperation with the movable plate, and the through hole of the movable plate is aligned with the through hole of the stationary plate when the movable plate abuts against one end of the position-limiting groove, and is misaligned with the through hole of the stationary plate when the movable plate abuts against the other end of the position-limiting groove.

9. The control device according to claim 5, wherein the through-beam photoelectric switch comprises a light projector and a light receiver, and the light projector and the light receiver are respectively arranged at two ends of a frame.

10. The control device according to claim 2, wherein the shutter comprises a stationary plate and a movable plate which both has a through hole for the light beam of the through-beam photoelectric switch to pass through; and the movable plate is connected to the trigger, and is movable under the actuation of the trigger to allow the through hole of the movable plate to be misaligned with the through hole of the stationary plate to block the light beam of the through-beam photoelectric switch.

11. The control device according to claim 10, wherein the movable plate has one end connected to the trigger and the other end connected to a return spring for driving the movable plate back to its original position.

12. The control device according to claim 11, wherein the shutter further comprises a position-limiting member for limiting a stroke of the movable plate.

13. The control device according to claim 12, wherein the position-limiting member is a position-limiting groove in cooperation with the movable plate, and the through hole of the movable plate is aligned with the through hole of the stationary plate when the movable plate abuts against one end of the position-limiting groove, and is misaligned with the through hole of the stationary plate when the movable plate abuts against the other end of the position-limiting groove.

14. The control device according to claim 10, wherein the through-beam photoelectric switch comprises a light projector and a light receiver, and the light projector and the light receiver are respectively arranged at two ends of a frame.

15. A patient table, comprising a frame and a pallet arranged on the frame, wherein the pallet is controlled by a control device of the pallet of the patient table, where the patient table has a control board for controlling movement of the patient table, and the pallet of the patient table has a manually operated push-pull portion, wherein the control device comprises a through-beam photoelectric switch, a shutter and a trigger connected to the shutter, the trigger is arranged on the push-pull portion to allow the shutter to be driven to move when a hand acts on the push-pull portion, to block a light beam of the through-beam photoelectric switch; the through-beam photoelectric switch is in signal connection with the control board of the patient table and is configured to send a signal for releasing the pallet to the control board of the patient table once the light beam of the through-beam photoelectric switch is blocked.

16. The patient table according to claim 15, wherein the trigger is embedded in the push-pull portion and has a gripping portion extending out of the push-pull portion, and the gripping portion is connected to the shutter.

17. The patient table according to claim 15, wherein the shutter comprises a stationary plate and a movable plate which both has a through hole for the light beam of the through-beam photoelectric switch to pass through; and the movable plate is connected to the trigger, and is movable under the actuation of the trigger to allow the through hole of the movable plate to be misaligned with the through hole of the stationary plate to block the light beam of the through-beam photoelectric switch.

18. The patient table according to claim 17, wherein the movable plate has one end connected to the trigger and the other end connected to a return spring for driving the movable plate back to its original position.

19. The patient table according to claim 18, wherein the shutter further comprises a position-limiting member for limiting a stroke of the movable plate; the position-limiting member is a position-limiting groove in cooperation with the movable plate, and the through hole of the movable plate is aligned with the through hole of the stationary plate when the movable plate abuts against one end of the position-limiting groove, and is misaligned with the through hole of the stationary plate when the movable plate abuts against the other end of the position-limiting groove.

20. The patient table according to claim 17, wherein the through-beam photoelectric switch comprises a light projector and a light receiver, and the light projector and the light receiver are respectively arranged at two ends of a frame.

* * * * *